United States Patent [19]

Goda et al.

[11] Patent Number: 5,352,821
[45] Date of Patent: Oct. 4, 1994

[54] 2,5-DICHLOROPHENYLTHIOGLYCOLIC ACID DERIVATIVE AND METHOD FOR ITS PRODUCTION

[75] Inventors: Hiroshi Goda; Nario Kimura; Naohiro Yoshikawa; Katsuhiko Yoshida, all of Hyogo, Japan

[73] Assignee: Sumitomo Seika Chemicals Co., Ltd., Hyogo, Japan

[21] Appl. No.: 19,906

[22] Filed: Feb. 19, 1993

Related U.S. Application Data

[62] Division of Ser. No. 824,313, Jan. 23, 1992, Pat. No. 5,210,287.

[30] Foreign Application Priority Data

Jan. 24, 1991 [JP] Japan .................................. 3-024027

[51] Int. Cl.$^5$ .......................................... C07C 323/62
[52] U.S. Cl. ................................................ 562/431
[58] Field of Search ................................. 562/55, 431

[56] References Cited

U.S. PATENT DOCUMENTS

3,440,288  4/1969  Hoffmann et al. .

FOREIGN PATENT DOCUMENTS

0212607  3/1987  European Pat. Off. .

OTHER PUBLICATIONS

Chemical Abstracts 68:59210A (1968).
Galat, J. American Chemical Society, 74, pp. 3890–3891 (1951).
Cecchetti et al., J. Medicinal Chemistry, 30, pp. 465–473 (1987).

*Primary Examiner*—Nicky Chan
*Attorney, Agent, or Firm*—Birch, Stewart, Kolasch & Birch

[57] ABSTRACT

The present invention is directed to novel 2,5-dichlorophenylthioglycolic acid derivative, a process for their production and a process for producing the desired product 2,5-dichlorophenylthioglycolic acid derived from said novel compounds. 2,5-dichlorophenylthioglycolic acid derivative of the present invention can be obtained by reacting 2,4,5-trichlorobenzensulfonates and thioglycolic acid in the presence of base, and said desired product can be obtained by desulfonating said compound in an aqueous solution of mineral acid. Novel 4-carboxymethylthio-2,5-dichlorobenzenesulfonates of the present invention can be used advantageously as an intermediate for the production of 2,5-dichlorophenylthioglycolic acid. The use of said intermediate makes it possible to obtain the desired product in a decreased process steps with high yield. In addition, it poses no problem of environmental pollution as pointed out with conventional methods because it uses no heavy metals.

13 Claims, No Drawings

2,5-DICHLOROPHENYLTHIOGLYCOLIC ACID DERIVATIVE AND METHOD FOR ITS PRODUCTION

This application is a divisional of copending application Ser. No. 07/824,313, filed on Jan. 23, 1992, now U.S. Pat. No. 5,210,287, the entire contents of which are hereby incorporated by reference.

FIELD OF THE INVENTION

The present invention relates to 2,5-dichlorophenylthioglycolic acid derivatives. More specifically, the invention relates to novel compound of 4-carboxymethylthio-2,5-dichlorobenzenesulfonates, methods for their production, and a method for producing 2,5-dichlorophenylthioglycolic acid derived from said novel compound.

2,5-dichlorophenylthioglycolic acid is a compound which is useful as an intermediate for thioindigo pigments, chemicals for the electronic industry, pharmaceuticals and agricultural chemicals Particularly, 4,4',7,7'-tetrachlorothioindigo derived from said compound is widely used as a pigment due to its high color fastness.

BACKGROUND OF THE INVENTION

There are some conventional methods for producing 2,5-dichlorophenylthioglycolic acid, including the following:

(a) the method in which 1,4-dichlorobenzene is sulfochlorinated with chlorosulfonic acid and then reduced to 2,5-dichlorothiophenol with zinc powder under acidic conditions, followed by reaction with monochloroacetic acid to yield 2,5-dichlorophenylthioglycolic acid (U.S. Pat. No. 3440288), (b) the method in which 2,5-dichloroaniline is diazotized and then reacted with thiourea in the presence of copper sulfate and subsequently hydrolyzed to 2,5-dichlorothiophenol, followed by reaction with monochloroacetic acid to yield 2,5-dichlorophenylthioglycolic acid (Ger. Offen. DE3715508), (c) the method in which 1,2,4-trichlorobenzene and sodium hydrosulfide are reacted in the presence of copper acetate catalyst in liquid ammonia solvent under increased pressure to yield 2,5-dichlorothiophenol, followed by reaction with monochloroacetic acid to yield 2,5-dichlorophenylthioglycolic acid [Kogyo Kagaku, 70, 1384 (1967)].

However, these known methods respectively have the following drawbacks.

In the method of (a) above, a large amount of waste effluent which contains harmful heavy metals poses a major problem of environmental pollution. In the method of (b) above, the copper compound used is difficult to dispose of as in (a) and the production efficiency is low; it is not an economic method of production. In the method of (c) above, liquid ammonia is difficult to handle and the copper compound used is difficult to dispose of, and additionally special equipment is required because the reaction is carried out under high pressure. Also, there is a problem of very low yield.

As stated above, all these known methods have various drawbacks and are not industrially advantageous, For this reason, attempts have been made to develop an industrially advantageous method for producing 2,5-dichlorophenylthioglycolic acid, but there is no satisfactory method.

SUMMARY OF THE INVENTION

It is an object of the present invention to provide a method for producing 2,5-dichlorophenylthioglycolic acid easily and economically using no harmful heavy metals.

It is another object of the present invention to provide a novel intermediate which serves well for the production of 2,5-dichlorophenylthioglycolic acid.

It is still another object of the present invention to provide a method for producing the intermediate.

Accordingly, the inventors found that the desired product 2,5-dichlorophenylthioglycolic acid can be prepared by reacting 2,4,5-trichlorobenzenesulfonates and thioglycolic acid in the presence of a base (Process A) to yield a novel 4-carboxymethylthio-2,5-dichlorobenzenesulfonate represented by formula (I), and desulfonating it using an aqueous solution of mineral acid (Process B). The inventors made further investigations based on this finding, and developed the present invention.

Accordingly, the present invention essentially relates to:

(1) novel 4-carboxymethylthio-2,5-dichlorobenzenesulfonates, (2) a method for producing novel 4-carboxymethylthio-2,5dichlorobenzenesulfonates characterized by reacting 2,4,5trichlorobenzenesulfonates and thioglycolic acid in the presence of a base, (3) a method for producing 2,5-dichlorophenylthioglycolic acid characterized by desulfonating 4-carboxymethylthio-2,5dichlorobenzenesulfonates using an aqueous solution of mineral acid, and (4) a method for producing 2,5-dichlorophenylthioglycolic acid characterized by reacting 2,4,5-trichlorobenzenesulfonates and thioglycolic acid in the presence of a base and subsequently reacting the reaction mixture with mineral acid or an aqueous solution of mineral acid.

The method for producing 2,5-dichlorophenylthioglycolic acid according to the present invention is a totally novel method and is characterized in that:

(1) the use of 2,4,5-trichlorobenzenesulfonates as a starting material offers improvement in the reactivity of the 4-position chlorine atom due to the strong electron attracting property of the sulfone group and thus makes reaction with thioglycolic acid in the presence of base easy and permits direct introduction of thioglycol group (Process A), and (Process A)

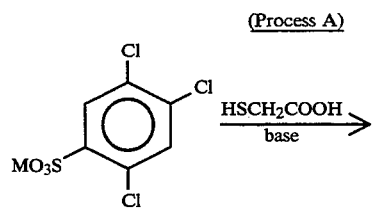

-continued
(Process A)

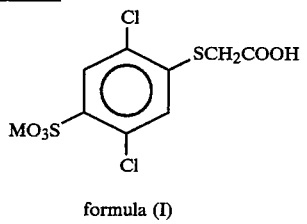

formula (I)

(wherein M represents hydrogen, sodium or potassium)

(2) the novel 4-carboxymethylthio-2,5-dichlorobenzenesulfonates thus obtained, which are 2,5-dichlorophenylthioglycolic acid derivatives, can easily be desulfonated to the desired 2,5-dichlorophenylthioglycolic acid by reacting with an aqueous solution of mineral acid due to the action of thioglycol group, which is an electron donor (Process B). The reaction proceeds with high yield in both processes.

In the of above-mentioned Process A, the 2,4,5-trichlorobenzenesulfonates used, as the starting material are 2,4,,5-trichlorobenzenesulfonic acid or, alkali metal salt thereof such as sodium, potassium or others of said sulfonic acid.

(Process B)

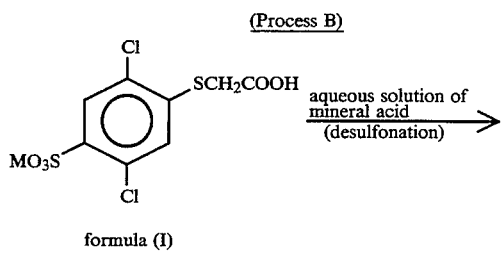

formula (I)

(wherein M represents hydrogen, sodium or potassium)

As stated above, the method of the present invention is a unique method utilizing the chemical nature of sulfone group and can be said to be both economically and industrially advantageous because the number of process steps are decreased and it gives a high yield of the desired product, 2,5-dichlorophenylthioglycolic acid. In addition, the method of the present invention is free of environmental pollution problems because it uses no heavy metals.

DETAILED DESCRIPTION OF THE INVENTION 2,4,5-trichlorobenzenesulfonates, the starting materials for the present invention, can easily be obtained by a known method, for example, by sulfonating 1,2,-trichlorobenzene. The reaction mixture obtained through the above sulfonation process can be used in Process A for the present invention.

Specifically, Process A is a process in which 2,4,5-trichlorobenzenesulfonates are reacted with thioglycolic acid in the presence of a base to yield novel 4-carboxymethylthio-2,5-dichlorobenzenesulfonates, which are derivatives of 2,5-dichlorophenylthioglycolic acid, with high yield.

Examples of bases include hydroxides of alkali metal, such as sodium hydroxide and potassium hydroxide, carbonates of alkali metal such as sodium carbonate and potassium carbonate and alcoholates of alkali metal, such as sodium methylate and sodium ethylate, with preference given to sodium hydroxide because it is less expensive.

When using sodium salt as the base, sodium 4-carboxymethylthio-2,5-dichlorobenzenesulfonate is obtained. When using potassium salt as the base, potassium 4-carboxymethylthio-2,5-dichlorobenzenesulfonate is obtained. Acidifying said obtained sodium salt or potassium salt by ion-exchange method yields 4-carboxymethylthio-2,5-dichlorobenzenesulfonic acid as shown below.

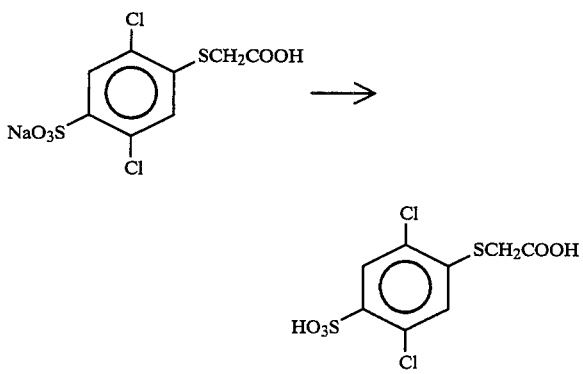

When using alkali metal salts of 2,4,5-trichlorobenzenesulfonic acid as the starting material, the same kind of alkali metal salt is preferably used as the base.

The amount of base used is normally in the range of 2.0 to 6.0 mol, preferably 3.0 to 5.5 mol per mol of 2,4,5-trichlorobenzenesulfonates. If the amount of base is less than 2.0 mol, the yield of the desired 4-carboxymethylthio-2,5-dichlorobenzenesulfonates decreases; if the amount of base used is more than 6.0 mol, no corresponding increase in yield is obtained so that it is economically disadvantageous.

The amount of thioglycolic acid used is normally in the range from 0.9 to 2.0 mol, preferably 1.0 to 1.5 mol per mol of 2,4,5-trichlorobenzenesulfonates. If the amount of thioglycolic acid is less than 0.9 mol, the yield of the desired 4-carboxymethylthio-2,5-dichlorobenzenesulfonates decreases; if the amount exceeds 2.0 mol, no corresponding increase in yield is obtained so that it is economically disadvantageous.

The reaction solvent used is not subject to limitation. Examples of reaction solvents which can be used for the present invention include water, alcohols such as methanol, ethanol, propanol, butanol and ethylene glycol, polar solvents such as N,N-dimethylformamide, N-methyl-2-pyrrolidone, dimethylsulfoxide and sulfolane and mixtures thereof, with preference given to water because it is economic.

Reaction temperature are is normally in the range from 70° to 250° C., preferably 90° to 180° C. Temperatures exceeding 250° C. results in a reduction in the yield of 4-carboxymethythio-2,5-dichlorobenzenesulfonates due to side reactions; when the reaction temperature is under 70° C., the reaction velocity obtained is too low for practical use.

The reaction proceeds under a normal pressure of 1 kg/cm² (hereinafter all figures for pressure are shown in absolute unit). In this case, a reaction time of 10 to 90 hours is required. When the reaction is carried out under increased pressure at increased temperature, the reaction time can be shortened. The pressure is normally under 20 kg/cm², preferably between 2 and 10 kg/cm². Under increased pressures exceeding 20 kg/cm², the reaction velocity is too high to control; therefore, such high pressures are undesirable from the viewpoint of operability.

Consequently, the reaction can be completed in any reaction time by selecting appropriate reaction pressure and temperature within the above-mentioned ranges, as described in the examples given below.

The 4-carboxymethylthio-2,5-dichlorobenzenesulfonates thus obtained can be isolated by an appropriately selected known means, such as filtration or extraction under acidic conditions.

The desired product 2,5-dichlorophenylthioglycotic acid can be obtained by heating and desulfonating the 4-carboxymethylthio-2,5-dichlorobenzenesulfonates obtained in aforementioned Process A in an aqueous solution of mineral acid (Process B).

Examples of the aqueous solution of mineral acid used in Process B include aqueous solutions of sulfuric acid, those of hydrochloric acid and those of phosphoric acid, with preference given to those of sulfuric acid. Although the concentration of the aqueous solution of mineral acid for the desulfonation varies depending on the type of the mineral acid, good results are obtained when the concentration is in the range of from 30 to 80%. Concentrations lower than 30% or higher than 80% are undesirable; if the concentration of the aqueous solution of mineral acid is lower than 30%, the reaction velocity is too low for practical use; if it exceeds 80%, the yield of the desired product 2,9-dichlorophenylthioglycolic acid decreases due to side reactions.

The amount of mineral acid used is normally in the range from 0.09 to 50 mol, preferably 0.1 to 30 mol per mol of 4-carboxymethylthio-2,-dichlorobenzenesulfonates. Amounts lower than 0.05 mol or higher than 50 mol are undesirable; if the amount is less than 0.05 mol, the reaction rate is too low; if the amount exceeds 50 mol, no corresponding reaction rate increase is obtained, and the amount of mineral acid to be disposed of increases.

Reaction temperatures for Process B are normally in the range from 100° to 200° C., preferably 120° to 160° C. Reaction temperatures exceeding 200° C. result in a reduction in the yield of the desired product 2,5-dichlorophenylthioglycolic acid, due to side reactions; if the reaction temperature is lower than 100° C., the reaction rate obtained is too low for practical use.

Process B requires no solvent, and an aqueous solution of mineral acid can be used as a solvent. When the amount of mineral acid is low, a solvent may be added. If used the solvent, type is not subject to limitation, as long as it is inert in the desulfonation reaction. Examples of such solvents include halogenated aromatic compounds, such as chlorobenzene, dichlorobenzene and trichlorobenzene, ethylene glycol derivatives such as diethylene glycol dimethyl ether and polar solvents, such as sulfolane.

The production of 2,9-dichlorophenylthioglycolic acid is carried out in Process B after isolating the 4-carboxymethylthio-2,5-dichlorobenzenesulfonates obtained in Process A, as stated above. In Process A, the 4-carboxymethylthio-2,5-dichlorobenzenesulfonates may also be used without isolation; mineral acid or an aqueous solution of mineral acid is added to the reaction mixture of Process A, followed by a desulfonation reaction in the next process (Process B). It is therefore possible to produce 2,5-dichlorophenylthioglycolic acid in a one-pot reaction. In this case, the amount of mineral acid used, reaction conditions and other factors are the same as above.

The 2,5-dichlorophenylthioglycolic acid thus obtained can easily be separated, by diluting the reaction mixture with water and then filtering it.

As stated above, according to the present invention, the desired product 2,5-dichlorophenylthioglycolic acid can easily be obtained by desulfonating in an aqueous solution of mineral acid the novel 4-carboxymethylthio-2,5-dichlorobenzenesulfonates, which are derivatives of 2,5-dichlorophenylthioglycolic acid obtained by reacting 2,4,5-trichlorobenzenesulfonates and thioglycolic acid in the presence of a base.

The novel 4-carboxymethylthio-2,5-dichlorobenzenesulfonates can be used advantageously as an intermediate for the production of 2,5-dichlorophenylthioglycolic acid. The use of said intermediate makes it possible to obtain the desired product 2,5-dichlorophenylthioglycolic acid with fewer process steps and high yields. The method of the present invention is thus both economically and industrially advantageous and poses no problem of environmental pollution as pointed out with conventional methods because it uses no heavy metals.

EXAMPLES

The present invention is hereinafter described in more detail by means of the following working examples, but the invention is not limited by these examples.

Example 1

To a 300 ml three-necked flask equipped with a stirrer, a thermometer and a condenser were charged 26.15 g (0.100 mol) of 2,4,5-trichlorobenzenesulfonic acid, 9.66 g (0.105 mol) of thioglycolic acid, 12.6 g (0.315 mol) of sodium hydroxide and 200 ml of water, followed by stirring at 100° C. for 10 hours. Then, after cooling to room temperature, the insoluble substances were filtered out. Then, the filtrate was acidified with concentrated hydrochloric acid. The resulting crystal was collected by filtration to yield 23.8 g of a crude crystal. This crude crystal was dissolved in methanol. After separation from the side product inorganic salts, the crystal was purified to yield 23.7 g of a white powder, which was identified as sodium 4-carboxymethylthio-2,5-dichlorobenzenesulfonate from the physical property data shown below. Its yield relative to 2,4,5-trichlorobenzenesulfonic acid was 70.0%.

The melting point, elemental analysis data, NMR spectrum data and IR spectrum data of sodium 4-carboxymethylthio-2,5dichlorobenzenesulfonate are shown below.

melting point: more than 300° C.

| elemental analysis | C | H | Cl | S | Na |
|---|---|---|---|---|---|
| found | 28.4% | 1.5% | 20.8% | 18.7% | 6.7% |
| calculated | 28.3% | 1.5% | 20.9% | 18.9% | 6.8% |

NMR(δppm, CD₃OD): 7.98(S, 1H), 7.46(S, 1H), 3.98(S, 2H) IR(cm⁻¹, KBr): 3500, 3000, 1730, 1220, 1190

Example 2

25.7 g of white powder was obtained in the same manner as in Example 1 except that the sodium hydroxide was replaced with 17.6 g (0.315 mol) of potassium hydroxide, followed by separation and purification. The white powder thus obtained was identified as potassium 4-carboxymethylthio-2,5-dichlorobenzenesulfonate from the physical property data shown below. The yield relative to 2,4,5-trichlorobenzenesulfonic acid was 72.5%.

melting point: more than 300° C.

| elemental analysis | C | H | Cl | S | K |
|---|---|---|---|---|---|
| found | 27.2% | 1.5% | 19.9% | 17.8% | 10.8% |
| calculated | 27.0% | 1.4% | 20.0% | 18.0% | 11.0% |

NMR(δppm, CD₃OD): 7.98(S, 1H), 7.46 (S, 1H), 3.98(S, 2H) IR(cm⁻¹, KBr:) 3500, 3000, 1730, 1220, 1190

Example 3

10.0 g of sodium 4-carboxymethylthio-2,5-dichlorobenzenesulfonate obtained in Example 1 was acidified by cation exchange resin. After separation and purification, 8.2 g of white powder was obtained. The white powder thus obtained was identified as 4-carboxymethylthio-2,5-dichlorobenzenesulfonic acid from the physical property data shown below.

melting point: more than 300° C.

| elemental analysis | C | H | Cl | S |
|---|---|---|---|---|
| found | 30.4% | 1.9% | 22.1% | 20.0% |
| calculated | 30.3% | 1.9% | 22.4% | 20.2% |

NMR(δppm, CD₃OD): 7.98(S, 1H), 7.46(S, 1H), 3.98(S,2H) IR(cm⁻¹, KBr): 3500, 3000, 1730, 1220, 1190

Example 4

To a 300 ml autoclave equipped with a stirrer and a thermometer were charged 12.6 g (0.315 mol) of sodium hydroxide and 200 ml of water, followed by addition of 26.15 g (0.100 mol) of 2,4,5-trichlorobenzenesulfonic acid and 9.66 g (0.105 mol) of thioglycolic acid and stirring at 150° C. under hermetic conditions for 6 hours. Through the reaction time pressure showed 5.0 kg/cm². After completion of the reaction, the reaction mixture was cooled to room temperature and then assayed by high performance liquid chromatography; it was found that 33.3 g of sodium 4-carboxymethylthio-2,5-dichlorobenzenesulfonate was produced. The reaction production ratio was 98.1% relative to 2,4,5-trichlorobenzenesulfonic acid.

Examples 5 through 8

Sodium 4-carboxymethylthio-2,5-dichlorobenzenesulfonate was obtained in the same manner as in Example 4 a except that reaction was carried out using the reaction pressures, reaction temperatures and reaction times shown in Table 1. The results are shown in Table 1

TABLE 1

| Exam. No. | reaction pressure (kg/cm²) | reaction temperature (°C.) | reaction time (Hr) | production ratio of sodium 4-carboxymethylthio-2,5-dichlorobenzenesulfonate |
|---|---|---|---|---|
| 5 | 1 | 100 | 15 | 83.6 |
| 6 | 2 | 120 | 6 | 84.7 |
| 7 | 10 | 170 | 1.5 | 98.0 |
| 8 | 14 | 180 | 0.8 | 97.8 |

Example 9

To a 300 ml three-necked flask equipped with a stirrer, a thermometer and a condenser were charged 33.9 g (0.10 mol) of sodium 4-carboxymethylthio-2,5-dichlorobenzenesulfonate obtained in Example 1 and 200 g(1.22 mol) of 60% sulfuric acid, followed by stirring at 140° to 145° C. for 10 hours. Then, after cooling to room temperature, the reaction mixture was diluted with water and then filtered, washed with water and dried to yield 22.2 g of a white powder of 2,5-dichlorophenylthioglycolic acid. Its yield relative to sodium 4-carboxymethylthio-2,5-dichlorobenzenesulfonate was 93.6%.

Example 10

Using the same procedure as in Example 9 except that the amount of 60% sulfuric acid was changed to 90 g (0.55 mol), 21.8 g of 2,5-dichlorophenylthioglycolic acid was obtained. Its yield relative to sodium 4-carboxymethylthio-2,5-dichlorobenzenesulfonate was 92.0%.

Example 11

22.1 g of the white powder, 2,5-dichlorophenylthioglycolic acid was obtained in the same manner as in Example 9 except that 31.7 g (0.10 mol) of 4-carboxymethylthio-2,5dichlorobenzenesulfonic acid obtained in Example 3 was used. Its yield relative to 4-carboxymethylthio-2,5-dichlorobenzenesulfonic acid was 93.2%.

Example 12

To the reaction mixture obtained in Example 4 was added 80 g (0.80 mol) of 98% concentrate sulfuric acid with stirring, followed by heating to 140° to 145° C. During this process, 150 g of water was distilled off. Stirring was continued for 10 more hours at this temperature. Then, after cooling to room temperature, the reaction mixture was diluted with water and then filtered, washed with water and dried to yield 21.1 g of a white powder of 2,5-dichlorophenylthioglycolic acid. Its yield relative to 2,4,5-trichlorobenzenesulfonic acid was 89.0%.

What is claimed is:

1. A process for producing 2,5-dichlorophenylthioglycolic acid which comprises the steps of:
    (a) reacting 2,4,5-trichlorobenzenesulfonates represented by the formula:

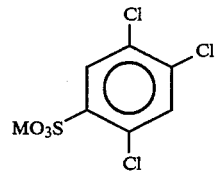

wherein M represents hydrogen, sodium or potassium, and thioglycolic acid in the presence of base; and (b). reacting the reaction mixture obtained in the step (a) with mineral acid or an aqueous solution of mineral acid.

2. A process according to claim 1 wherein said base is sodium hydroxide.

3. A process according to claim 1 wherein said base is potassium hydroxide.

4. A process according to claim 1 wherein the amount of said base used is 2.0 to 6.0 mol per mol of 2,4,5-trichlorobenzenesulfonates.

5. A process according to claim 1 wherein the reaction of step (a) proceeds under the pressure of not more than 20 kg/cm$^2$.

6. A process according to claim 1 wherein said aqueous solution of mineral acid is aqueous sulfate solution.

7. A process according to claim 1 wherein the amount of said aqueous solution of mineral acid used is 0.05 to 50 mol per mol of 4-carboxymethylthio-2,5-dichlorobenzenesulfonates.

8. A process according to claim 1 wherein the reaction of step (a) proceeds at a temperature from 70°–250° C. and the reaction proceeds at a pressure from 2–10 kg/cm$^2$.

9. A process according to claim 8 wherein the reaction proceeds at a temperature from 90°–180° C.

10. A process according to claim 1 wherein the amount of said thioglycolic acid used is 0.9 to 2.0 mole per mole of 2,4,5-trichlorobenzenesulfonates.

11. A process according to claim 4 wherein the amount of said base used is 3.0 to 5.5 moles per mole of 2,4,5-trichlorobenzenesulfonates.

12. A process according to claim 1 wherein the reaction of step (b) proceeds at a temperature from 100°–200° C.

13. A process according to claim 12 wherein the reaction proceeds at a temperature from 120°–160° C.

* * * * *